United States Patent [19]

Scott et al.

[11] Patent Number: 4,736,844

[45] Date of Patent: Apr. 12, 1988

[54] CONTAINER FOR THE DISPOSAL OF SHARPS

[75] Inventors: Stephen D. Scott, Lancashire; June M. Redstone, London, both of England

[73] Assignee: Nuffield Nursing Homes Trust, London, England

[21] Appl. No.: 82,610

[22] Filed: Aug. 7, 1987

[51] Int. Cl.[4] .................. B65D 85/24; B65D 81/36
[52] U.S. Cl. ................................................. 206/370
[58] Field of Search ............... 206/349, 370, 570, 363, 206/366

[56] References Cited

U.S. PATENT DOCUMENTS

| | | | |
|---|---|---|---|
| 4,106,620 | 8/1978 | Brimmer et al. | 206/363 |
| 4,168,777 | 9/1979 | Gaskell et al. | 206/370 X |
| 4,373,629 | 2/1983 | Ulin et al. | 206/370 X |
| 4,466,539 | 8/1984 | Frauenhoffer | 206/370 |
| 4,626,971 | 12/1986 | Schultz | 206/370 X |
| 4,637,513 | 1/1987 | Eldrige, Jr. | 206/370 |

Primary Examiner—William Price

Attorney, Agent, or Firm—Sughrue, Mion, Zinn, Macpeak and Seas

[57] ABSTRACT

A device for enabling the safe disposal of contaminated used disposable blades, needles, and other sharps resulting from surgery or medical treatment comprises a container (1) having two compartments, a first, closed compartment (2) including a slot (16) and a re-entrant wall portion (12) and a second compartment (3) including a hinged lid (4). Means (8, 9) are provided inside the second compartment (3) securely to hold used needles (22, 23, 24) and a catch (7) is provided to hold the lid (4) of the second compartment (3) closed. The slot (16) and re-entrant wall portion (12) enable a used blade to be inserted into the slot (16) with the re-entrant wall portion accommodating a handle upon which the used blade is mounted and a disarming unit (14, 15) is located adjacent the slot (16) and re-entrant wall portion (12) to remove the blade from the handle. At least part of the wall (10) of the first compartment (2) is transparent to enable the contents of the first compartment (2) to be inspected and counted.

8 Claims, 2 Drawing Sheets

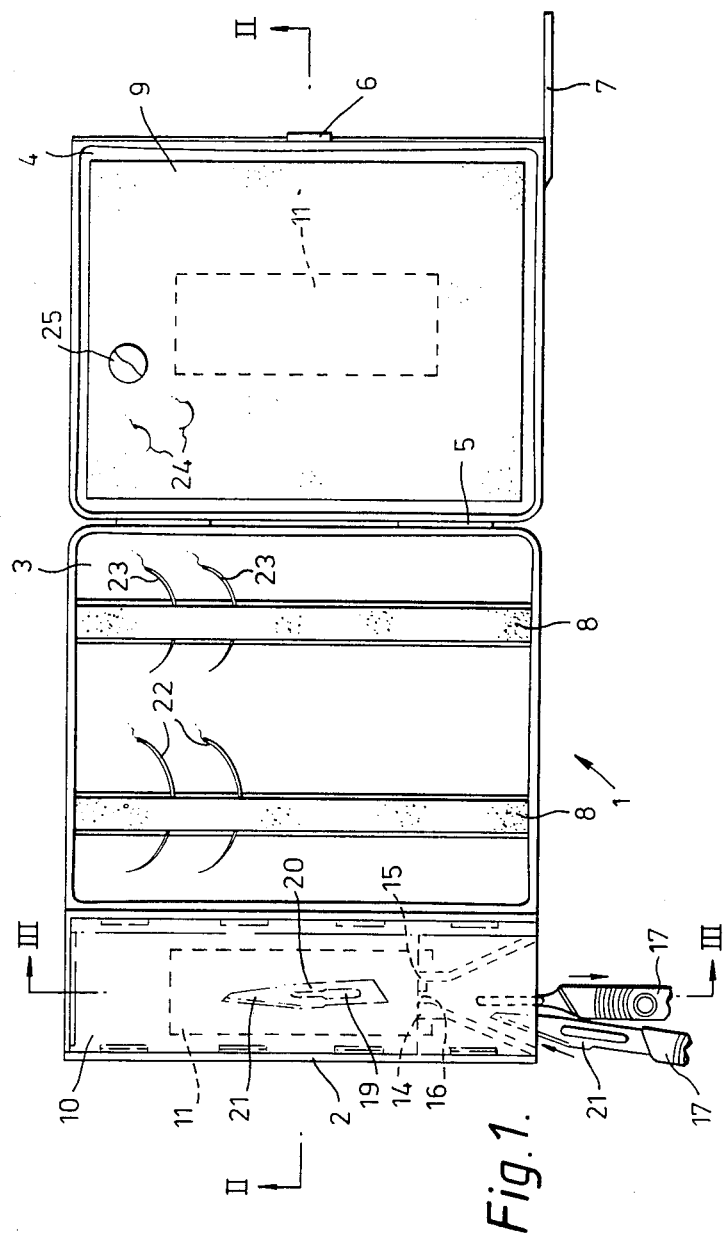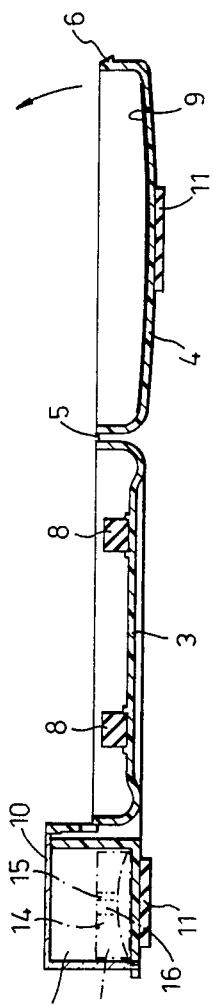

CONTAINER FOR THE DISPOSAL OF SHARPS

During surgery and medical treatment blades such as those attached to scalpels and other cutting instruments, needles such as hypodermic needles and suture needles, and other sharp debris which are known collectively as sharps, are produced. Frequently the sharps are contaminated with bodily fluids of the patient being treated. Such contaminated sharps are a particular source of danger in a hospital environment. Not only do they include sharp edges and penetrating points both of which can inflict injury but, since they are contaminated and may be contaminated with a life threatening virus or bacteria, the risks involved in their subsequent handling are greater. At present many hospitals do not have a reliable way of safely disposing of the sharps that have been used during a surgical operation or medical treatment.

According to this invention a device for enabling the safe disposal of contaminated used disposable blades, needles, and other sharps comprises a container having two compartments, a first, closed compartment including a slot and a re-entrant wall portion to enable a used blade to be inserted into the slot with the re-entrant wall portion accommodating a handle upon which the used blade is mounted and a disarming unit adjacent the slot and re-entrant wall portion to remove the blade from the handle, at least part of the wall of the first compartment being transparent to enable the contents of the first compartment to be inspected and counted, and a second compartment including a hinged lid, means inside the second compartment securely to hold used needles and a catch to hold the lid of the second compartment closed.

Typically surgical blades include a key hole shaped slot and they are mounted on the handle by inserting a key on the handle through the larger region of the key hole shaped slot and then urging the blade onto the handle until the heel of the blade snaps over the key or engages an abutment. This moves the narrower portion of a key hole shaped slot into a secure location beneath the key to hold the blade firmly on the handle. The disarming unit enables the blade to be removed from the handle by reversing the above sequence of operations or it may remove the blade from the handle by merely snapping it off.

In the first case the disarming unit preferably includes a detent arranged to engage the heel of the blade to lift it away from the key and hold the blade in position in the slot whilst the user pulls the handle away from the blade until the key on the handle is aligned with enlarged portion of the key hole shaped slot to enable the key to be removed from the key hole shaped slot. The detent preferably includes opposed projections which may also define the sides of the slot, one of which is arranged to engage the heel of the blade when the blade is inserted into the slot. Movement of the free end of the handle then causes the handle to rotate about the other of the projections and the one of the projections to bend the heel of the blade to lift it over the key of the handle. As the handle is withdrawn the heel of the blade engages the other projections and allows the handle to be withdrawn whilst the blade is held in position by the other projection. The used and contaminated blade is received by the first compartment and the handle is withdrawn from the re-entrant wall portion.

Preferably the second compartment includes an adhesive surface. This may be provided on the hinged lid of the second compartment and this adhesive surface is used to locate and hold securely irregularly shaped sharps such as the remains of a broken ampoule or small swabs such as pledgelets, peanut sponges and, for example, very small needles, hypodermic needles and used safety pins. The means securely to hold used needles is preferably formed by one or more strips of foamed plastics material which are fixed to the inside wall of the second compartment and into which the needles are threaded during and after use.

The catch on the lid of the second compartment is preferably one which, after having been closed, cannot easily be released. When the wall of the second compartment is resilient, the catch may be formed by formations one of which includes an inclined ramp surface and an abutment surface and the other of which includes an abutment surface. As the lid is closed, the ramp surface rides over the other formation so distorting the side walls of the second compartment until the lid is completely closed whereupon the catch snaps shut with the resilience of the walls moving the abutment surfaces into contact with one another to hold the lid closed. Alternatively, the catch may include one part having a conical head mounted on a stem with a smaller diameter than the maximum diameter of the head to provide an annular shoulder behind the head and the other part having an aperture with a resilient margin. The two parts are formed separately on the body and lid. In this case, as the lid is closed the head passes through the aperture stretching its margin until the lid is completely closed and, at this point, the resilient margin of the aperture contracts to engage the annular shoulder behind the head to hold the lid shut.

Preferably the outside surface of the lid and the base of the container include adhesive strips with a peel-off backing to allow the device to be adhered to, for example, the drapes of an instrument trolley, so that it is held securely in position during use.

The slot in the wall of the first compartment may be located inside the second compartment or be covered by at least part of the lid of the second compartment so that, once the lid is closed, the lid or an extension of it covers the slot in the wall of the first compartment and so prevents any possibility of used blades escaping from the first compartment via the slot.

A particular example of this device in accordance with this invention will now be described with reference to the accompanying drawings in which:

FIG. 1 is a plan of the device with the lid of the second compartment open;

FIG. 2 is a cross section through the device taken along the line II—II shown in FIG. 1, with the lid of the second compartment open;

Figure 3:
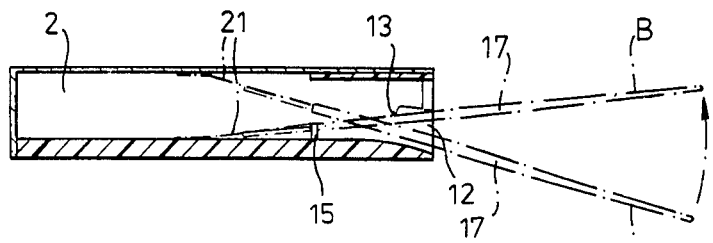
FIG. 3 is a longitudinal section through the first compartment taken along the lines III—III shown in FIG. 1 illustrating the operation of the disarming unit; and, FIG. 4 is an enlarged detail section of the catch with the lid about to close.

The device comprises a container 1 having a first compartment 2 and a second compartment 3. A lid 4 is joined to the remainder of the second compartment 3 by a membrane hinge 5 and a catch 6 is provided to hold the lid 4 closed. An extension flap 7 on the lid 4 covers the end of the first compartment 2 when the lid is closed. Two dense foam strips 8 are fixed to the inside of the second compartment 3 and an adhesive layer 9 is formed inside the lid 4. The compartment 1 includes a transparent face 10 to enable its contents to be inspected and counted and adhesive pads 11 are provided on the outside surface of a base of the second compartment 3 and the lid 4 to enable the device to be adhered to a surface in use. A check list (not shown) is usually included in the container 1 to enable all of the sharps introduced into an operating field to be recorded and to facilitate a subsequent count of them. The first compartment 2 includes a re-entrant body portion 12 a base of which includes a slot 13 seen best in FIG. 3. Projections 14 and 15 are located at the innermost ends of the re-entrant portion 12 and a further slot 16 is defined between them.

Typically a scalpel or other knife used in surgery comprises a handle 17 having a narrow head 18. The head 18 includes a key which fits into an enlarged portion 19 of a key hole shaped slot 20 of a blade 21. To use the disarming unit the scalpel is inserted into the re-entrant portion 12 with the blade 21 extending through the slot 13 in the position shown as A in FIG. 3. The handle 17 is then raised whilst, at the same time, pressing down on the forward end of the handle. The handle 17 turns around one side of the slot 13 into the position B with the head 18 of the handle being received in the further slot 16. The projections 14 and 15 engage the heel of the blade 21 causing it to bend and disengage from the rear of the key on the head 18 of the handle 17. The handle 17 is then withdrawn and, the raised heel of the blade 21 engages the one side of the slot 13. Further withdrawal of the handle 17 releases the blade 17 from the key on the head 18. As the handle 17 is removed from the re-entrant portion 12 the blade 21 is released from the handle 17 and is received in the first compartment 2.

Suture needles 22 and 23 and hypodermic syringe needles (not shown) are threaded into the dense foam strips 8 in the second compartment 3. Very small suture needles 24 pledgelets 25 and other small items are adhered to the adhesive layer 9 in the lid 4.

At the conclusion of the surgical operation or other medical treatment the used sharps and other items which have accumulated in the device are counted and compared with those entered on the check list to make sure that they are all accounted for and, if they are, the lid 4 is closed. The container 1 containing the sharps and other items can then be handled safely with no possibility of any of them coming into contact with anybody handling the package. The entire container 1 and contents is incinerated.

Figure 4:
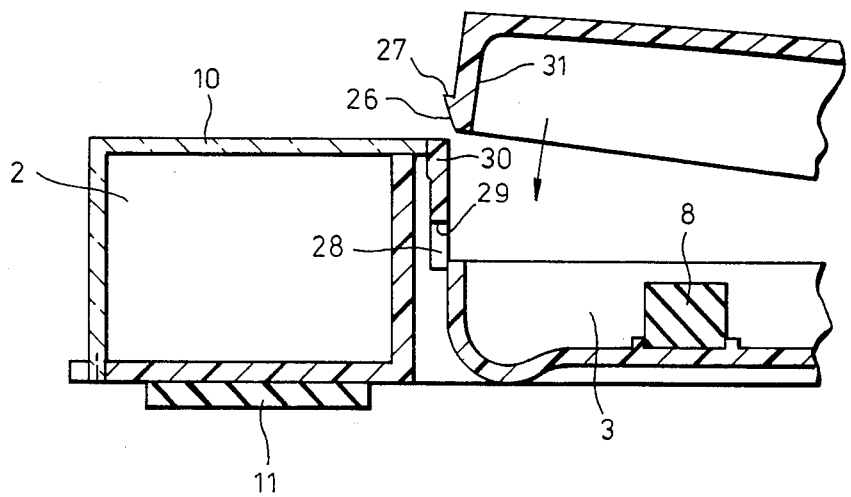

The catch is shown in more detail in FIG. 4 and comprises an outwardly included ramp surface 26 terminating in a first abutment surface 27 formed on the rim of the lid 4 and a co-operating slot 28 including a second abutment surface 29. As the lid 4 is shut to close the second compartment 3 the ramp surface rides over a wall 30 of the compartment 3 and, so doing distorts the side wall 31 of the lid 4. When the lid 4 is completely closed the distorted side wall 31 snaps back as the ramp surface 26 and first abutment surface 27 enter the slot 28 and the first 27 and second 29 abutment surfaces engage to hold the lid 4 closed. The extension on the lid 4 covers the re-entrant portion 12 of the first compartment 2 to ensure that no blades can escape from the first compartment 2 through the slot 16.

Typically the container 1 is sterilized before use, for example by irradiation, so that it is sterile before it is bought into the operating field. The container 1 is made from a material which is capable of incineration and typically it is made by injection moulding from a thermoplastics material.

We claim:

1. A device for enabling the safe disposal of contaminated used disposable blades, needles and other sharps said device comprising a container, means defining first and second compartments in said container, said first compartment being closed and including means defining an entry slot, a re-entrant wall portion to enable a used blade, which is mounted on a handle, to be inserted into said slot with said re-entrant wall portion accommodating said handle, a disarming unit adjacent said slot and said re-entrant wall portion for removing said blade from said handle, and a transparent wall portion to enable the contents of said first closed compartment to be inspected and counted, and said second compartment including a lid, means hinging said lid to said compartment, means inside said second compartment securely to hold used needles, and catch means to hold said lid of said second compartment closed.

2. A device as claimed in claim 1, in which said disarming unit includes a detent for engaging a heel portion of said blade to lift said blade away from a key on said handle and hold said blade in position in said slot whilst said handle is pulled away from said blade until said key on said handle is aligned with an enlarged portion of a key hole in said blade to enable said key to be removed from said key hole.

3. A device as claimed in claim 2, in which said detent further comprises opposed projections which define said slot of said first compartment, one of said projections being arranged to engage said heel of said blade when said blade is inserted into said slot to bend said heel to lift said blade over said key of said handle, and the other of said projections being arranged to engage said heel of said blade to prevent said blade being withdrawn from said slot as said handle is withdrawn.

4. A device as claimed in claim 1 or claim 2, in which said second compartment includes means defining an adhesive surface therein.

5. A device as claimed in claim 1 or claim 2, in which said means for securely holding said needles includes at least one strip of foamed plastics material and means fixing said strip to the inside of said second compartment.

6. A device as claimed in claim 1 or claim 2, in which said lid of said second compartment is resilient and in which said catch means includes means defining an inclined ramp surface, means defining a first abutment surface on said lid and means defining a second abutment surface on the bottom of said second compartment.

7. A device as claimed in claim 1 or claim 2, in which the outside surface of said lid and the bottom of said second compartment include adhesive strips and a peel-off backing on said strips.

8. A device as claimed in claim 1 or claim 2, in which means forming part of said lid covers said slot of said first compartment when said lid is closed whereby used blades are prevented from escaping from said first compartment through said slot.

* * * * *